United States Patent [19]

Pittet et al.

[11] Patent Number: 4,585,663
[45] Date of Patent: Apr. 29, 1986

[54] FLAVORING WITH GEM DITHIOETHERS OF PHENYLALKANES

[75] Inventors: Alan O. Pittet, Atlantic Highlands; Ranya Muralidhara, Fair Haven; Domenick Luccarelli, Jr., Neptune; Kevin P. Miller, Middletown; Manfred H. Vock, Locust, all of N.J.

[73] Assignee: International Flavors & Fragrances Inc., New York, N.Y.

[21] Appl. No.: 747,448

[22] Filed: Jun. 21, 1985

[51] Int. Cl.$^4$ .................. A23L 1/226; A23L 1/235
[52] U.S. Cl. ................................ 426/535; 568/57
[58] Field of Search ............................ 426/535; 568/57

[56] References Cited
U.S. PATENT DOCUMENTS
4,504,508  3/1985  Pittet et al. ........................ 426/535

Primary Examiner—Joseph Golian
Attorney, Agent, or Firm—Arthur L. Liberman

[57] ABSTRACT

Described are gem dithioethers of phenylalkanes defined according to the structure:

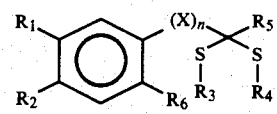

wherein $R_1$, $R_2$, $R_3$, $R_4$, $R_5$ and $R_6$ are each the same or different and each represents hydrogen or $C_1$–$C_3$ lower alkyl; X represents 1,1-ethylidene, 1,1-propylidene or 2,2-propylidene and N represents 0 or 1 with the provisos (i) when N is 0, $R_5$ is $C_1$–$C_3$ lower alkyl; and
(ii) when N=1, $R_5$ is hydrogen and uses thereof in augmenting or enhancing the aroma or taste of foodstuffs.

1 Claim, 2 Drawing Figures

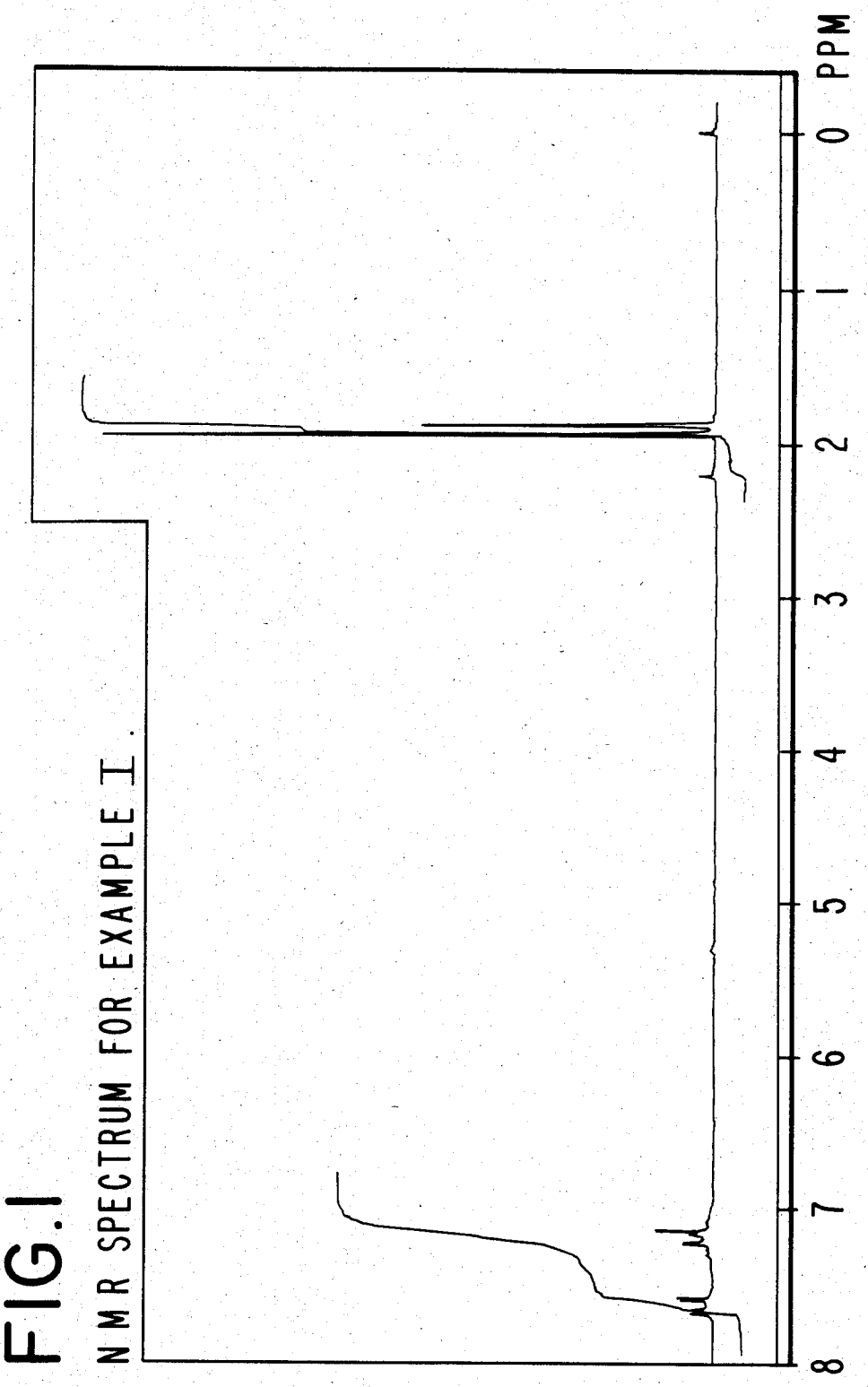

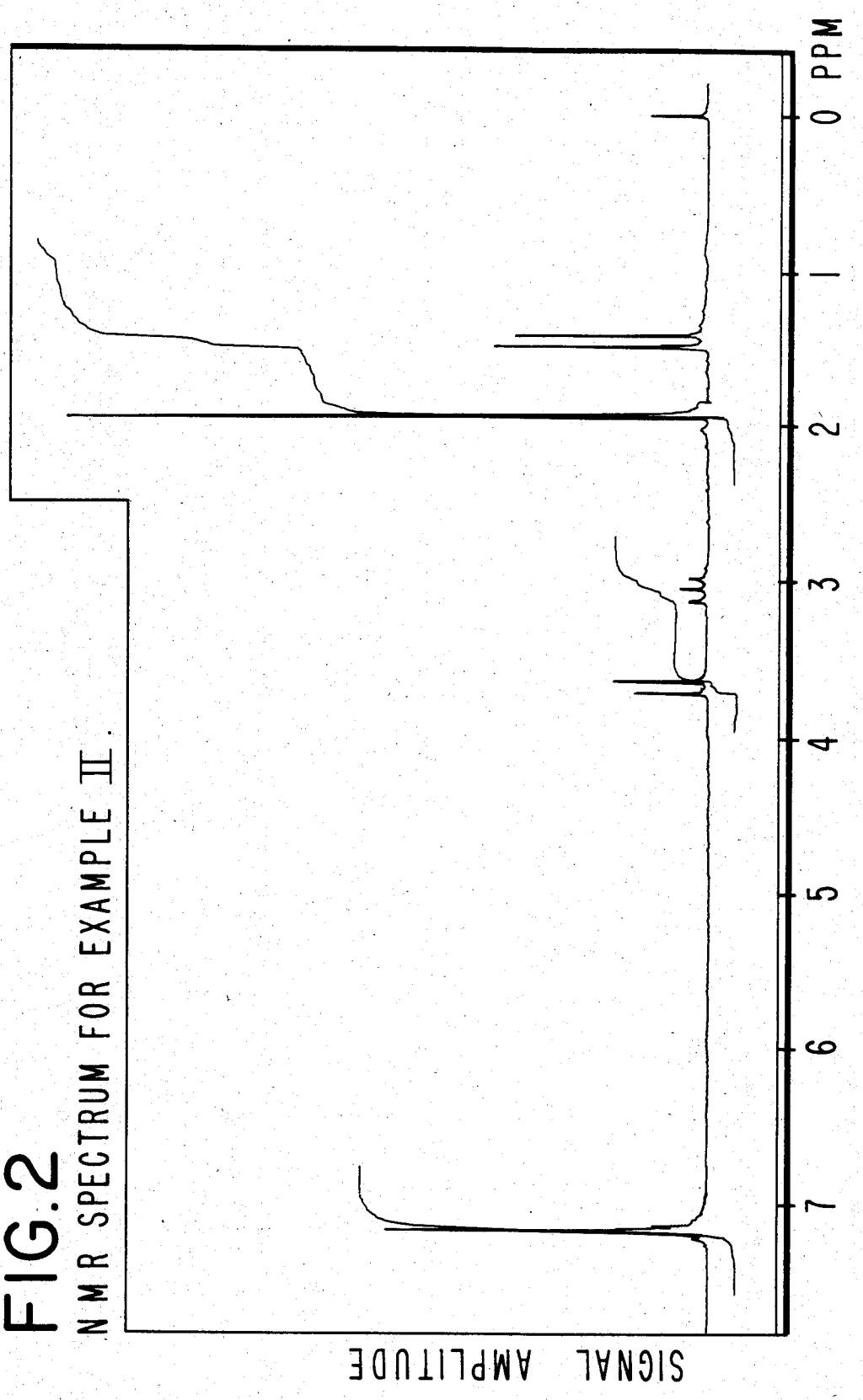
FIG. 2 NMR SPECTRUM FOR EXAMPLE II.

FLAVORING WITH GEM DITHIOETHERS OF PHENYLALKANES

BACKGROUND OF THE INVENTION

This invention provides gem dithioethers of phenylalkanes defined according to the generic structure:

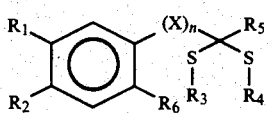

wherein $R_1$, $R_2$, $R_3$, $R_4$, $R_5$ and $R_6$ are each the same or different and each represents hydrogen or $C_1$–$C_3$ lower alkyl; X represents 1,1-ethylidene, 1,1-propylidene or 2,2-propylidene and N represents 0 or 1 with the provisos:

(i) when N is 0, $R_5$ is $C_1$–$C_3$ lower alkyl; and
(ii) when N=1, $R_5$ is hydrogen and uses thereof in augmenting or enhancing the aroma or taste of foodstuffs.

Artificial flavoring agents for foodstuffs have received increasing attention in recent years. In many areas, such food flavoring agents are preferred over natural flavoring agents at least in part because of the uniform flavor that may be so obtained. For example, natural food flavoring agents such as extracts, essences, concentrates and the like are often subject to wide variation due to changes in the quality, type and treatment of the raw materials. Such variation can be reflected in the end product and results in unreliable flavor characteristics and uncertainty as to consumer acceptance and cost. Additionally, the presence of the natural product in the ultimate food may be undesirable because of increased tendency to spoil. This is particularly troublesome in convenience and snack food usage where such products as dips, soups, chips, prepared dinners, canned foods, sauces, gravies and the like are apt to be stored by the consumer for some time prior to use.

The fundamental problem in preparing artificial flavoring agents is that of achieving as nearly as possible a true flavor reproduction. This generally proves to be a difficult task since the mechanism for flavoring development in many foods is not understood. This is notable in products having tropical fruit flavors, dairy flavors and cooked bean flavors.

Reproduction of onion, durian, tropical fruit, cheesy, beany, raw peanut, cooked vegetable and hydrolyzed vegetable protein-like aroma and taste profiles has been the subject of a long and continuous search by those engaged in the production of foodstuffs. The severe shortage of foods, especially protein foods, in many parts of the world has given rise to the need for utilizing non-meat sources of proteins and making such proteins as palatable and as meat-like as possible. Hence materials which will closely simulate or exactly reproduce the flavor and aroma of tropical fruits, dairy products and cooked bean flavored foodstuffs are required.

The use of dithio acetals in augmenting or enhancing the aroma or taste of foodstuffs is known in the art. Thus, U.S. Pat. No. 4,464,408 issued on Aug. 7, 1984 describes methyl substituted 2-(2,6-dimethyl-1-5,-heptadienyl)-1,3-dithiolanes defined according to the structure:

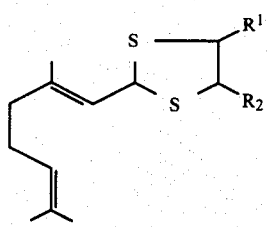

wherein $R_1$ and $R_2$ are the same or different and each represents methyl or hydrogen with the proviso that at least one of $R_1$ and $R_2$ is methyl and uses thereof in augmenting or enhancing the aroma or taste of foodstuffs.

Furthermore, U.S. Pat. No. 4,504,508 issued on Mar. 12, 1985 describes phenyl mercaptals defined according to the generic structure:

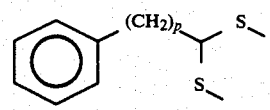

wherein p represents 0 or 1 and uses thereof in augmenting or enhancing the aroma or taste of foodstuffs.

The gem dithioethers of phenylalkanes of our invention in comparison with the compounds of the prior art have unexpected, unobvious and advantageous organoleptic properties concerning augmenting or enhancing the aroma or taste of foodstuffs.

BRIEF DESCRIPTION OF THE DRAWINGS

FIG. 1 is the NMR spectrum for the compound having the structure:

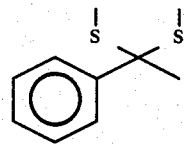

prepared according to Example I (Conditions: Field strength: 100 MHz; Solvent: $CFCl_3$I.

FIG. 2 is the NMR spectrum for the compound having the structure:

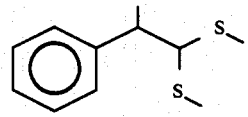

produced according to Example II (Conditions: Field strength: 100 MHz; Solvent: $CFCl_3$).

THE INVENTION

The present invention provides novel gem dithioethers of phenylalkanes having the structure:

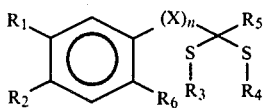

wherein $R_1$, $R_2$, $R_3$, $R_4$, $R_5$ and $R_6$ are each the same or different and each represents hydrogen or $C_1$–$C_3$ lower alkyl; X represents 1,1-ethylidene, 1,1-propylidene or 2,2-propylidene and N represents 0 or 1 with the provisos (i) when N is 0, $R_5$ is $C_1$–$C_3$ lower alkyl; and
(ii) when N=1, $R_5$ is hydrogen as well as methods for augmenting or enhancing or modifying the organoleptic properties (e.g., the taste and aroma of foodstuffs.

The gem dithioethers of phenylalkanes of our invention augment or enhance tropical fruit, dairy and cooked bean flavored foodstuffs. The gem dithioethers of phenylalkanes of our invention provide onion, durian, tropical fruit, cheesy, sulfury, beany, raw peanut, cooked vegetable and hydrolyzed vegetable protein-like aroma and the taste nuances.

The gem dithioethers of phenylalkanes of our invention having the structure:

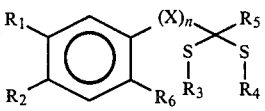

wherein $R_1$, $R_2$, $R_3$, $R_4$, $R_5$ and $R_6$ are each the same or different and each represents hydrogen or $C_1$–$C_3$ lower alkyl; X represents 1,1-ethylidene, 1,1-propylidene or 2,2-propylidene and N represents 0 or 1 with the provisos that:

(i) when N is 0, $R_5$ is $C_1$–$C_3$ lower alkyl; and
(ii) when N=1, $R_5$ is hydrogen.

may be prepared by reacting a carbonyl-containing phenyl substituted derivative defined according to the structure:

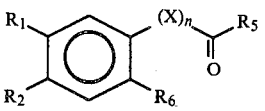

with one or both of the following mercaptans:

$R_4SH$ and/or $R_3SH$ wherein $R_1$, $R_2$, $R_3$, $R_4$, $R_5$, $R_6$, X and N are defined, supra according to the reaction:

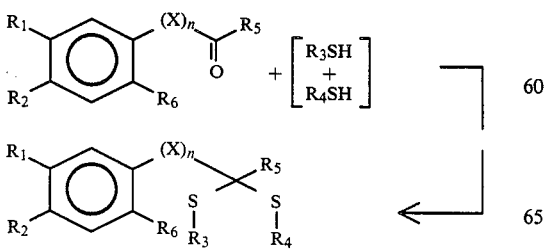

exemplified by the reactions:

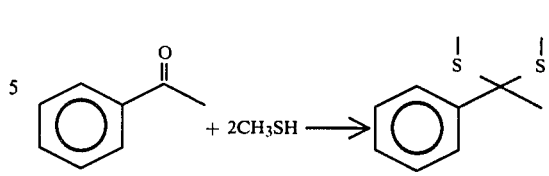

and

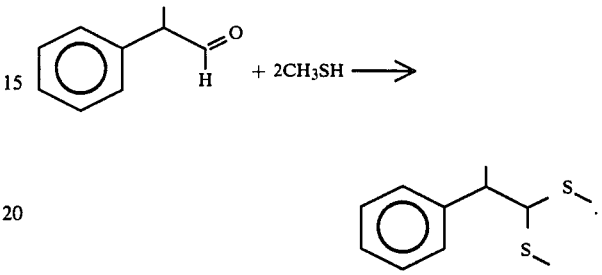

The reaction takes place by bubbling methyl mercaptan into a mixture of carbonyl derivative having the structure:

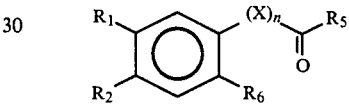

in the presence of a solvent and protonic acid catalyst at a temperature in the range of from about 0° C. up to about +10° C. Examples of protonic acid catalyst are paratoluene sulfonic acid, zylene sulfonic acid, methane sulfonic acid, phosphoric acid and concentrated sulfuric acid. As stated, supra the reaction takes place in the presence of a solvent which is inert to both the reactants and the reaction products. Preferred solvents are cyclohexane and methylene dichloride. Of course since the reaction products are used in augmenting or enhancing the aroma or taste of foodstuffs, the solvents must be completely removed prior to utilization of the resulting gem dithioethers of phenylalkanes for their intended uses. The reaction takes places over a reasonable period of time, e.g., 6–12 hours at atmospheric pressure.

Examples of the products of our invention and their organoleptic properties are as follows:

TABLE I

| Structure of Product of Invention | Organoleptic Properties |
|---|---|
| The compound having the structure:<br><br>prepared according to Example I. | An onion, durian, tropical fruit, cheesy and sulfury aroma profile at 0.1 ppm causing it to be useful in tropical fruit flavored foodstuffs and cheese and dairy foodstuffs. |

TABLE I-continued

| Structure of Product of Invention | Organoleptic Properties |
|---|---|
| The compound having the structure: (phenyl-CH(CH₃)-CH(S-)(S-)) prepared according to Example II. | A beany, raw peanut, cooked vegetable and hydrolyzed vegetable protein-like aroma and taste profile at 0.2 ppm causing it to be useful in cooked bean flavored foodstuffs. |

At the end of the reaction as stated, supra, the reaction product is extracted from the reaction mass or the reaction mass is washed, for example, with saturated sodium chloride. The reaction product is then distilled preferably by means of vacuum distillation.

Thus, gem dithioethers of phenylalkanes produced according to our invention can be used to alter, vary, fortify, modify, enhance or otherwise improve the organoleptic properties, including flavor and/or aroma, of a wide variety of materials which are ingested, consumed or otherwise organoleptically sensed.

The term "alter" in its various forms will be understood herein to mean the supplying or imparting a flavor character or note to an otherwise bland, relatively tasteless substance, or augmenting an existing flavor characteristic where the natural flavor is deficient in some regard, or supplementing the existing flavor or aroma impression to modify the organoleptic character. The materials which are so altered are generally referred to herein as consumable materials.

Such gem dithioethers of phenylalkanes of our invention are accordingly useful in flavoring compositions. Flavoring compositions are hereintaken to mean those which contribute a part of the overall flavor impression by supplementing or fortifying a natural or artificial flavor in a material, as well as those which supply substantially all the flavor and/or aroma character to a consumable article.

The term "foodstuff" as used herein includes both solid and liquid ingestible materials for man or animals, which materials usually do, but need not have nutritional value. Thus foodstuffs include meats, gravies, soups, convenience foods, malt and other alcoholic or non-alcoholic beverages, milk and dairy products, nut butters such as peanut butter and other spreads, seafoods including fish, crustaceans, mollusks and the like, candies, breakfast foods, baked goods, vegetables, cereal, soft drinks, snack foods, dog and cat foods, other veterinary products, and the like.

When the gem dithioethers of phenylalkanes according to this invention are used in a food flavoring composition, they can be combined with conventional flavoring materials or adjuvants. Such co-ingredients or flavoring adjuvants are well known in the art for such use and have been extensively described in the literature. Apart from the requirement that any such adjuvant material is ingestibly acceptable, and thus non-toxic or otherwise non-deleterious, conventional materials can be used and broadly include other flavor materials, vehicles, stabilizers, thickeners, surface active agents, conditioners and flavor intensifiers.

Examples of preferred co-flavoring adjuvants are:
Methyl thiazole alcohol(4-methyl-5-β-hydroxyethyl thiazole);
2-Methyl butanethiol;
4-Mercapto-2-butanone;
3-Mercapto-2-pentanone;
1-Mercapto-2-propanone;
Benzaldehyde;
Furfural;
Furfuryl alcohol;
2-Mercapto propionic acid;
Alkyl pyrazine;
Methyl pyrazine;
2-Ethyl-3-methyl pyrazine;
Polysulfides;
Dipropyl disulfide;
Methyl benzyl disulfide;
Alkyl thiophenes;
2-Butyl thiophene;
2,3-Dimthyl thiophene;
5-Methyl furfuryl
Acetyl furan;
2,4-Decadienal;
Guiacol;
Phenyl acetaldehyde;
Delta-Decalactone;
d-Limonene;
Acetoin;
Amyl acetate;
Maltol;
Ethyl butyrate;
Levulinic acid;
Piperonal;
Ethyl acetate;
n-Octanal;
n-Pentanal;
Hexanal;
Diacetyl;
Monosodium glutamate;
Monopotassium glutamate;
Sulphur-containing amino acids, e.g., cysteine;
Hydrolyzed vegetable protein;
2-Methylfuran-3-thiol;
2-Methyldihydrofuran-3-thio;
2,5-dimethylfuran-3-thiol;
Hydrolyzed fish protein; and
Tetramethyl pyrazine.

The gem dithioethers of phenylalkanes or the compositions incorporating them, as mentioned above, can be combined with one or more vehicles or carriers for adding them to the particular product. Vehicles can be edible or otherwise suitable materials such as ethyl alcohol, propylene glycol, water and the like. Carriers include materials such as gum arabic, carrageenan, other gums and the like. The gem dithioethers of phenylalkanes according to this invention can be incorporated with the carriers by conventional means such as spray-drying, drum drying and the like. Such carriers can also include materials for coacervating the gem dithioethers of phenylalkanes (and other flavoring ingredients, as present) to provide encapsulated products. When the carrier is an emulsion, the flavoring composition can also contain emulsifiers such as mono- and diglycerides or fatty acids and the like. With these carriers or vehicles, the desired physical form of the composition can be prepared.

The quantity of gem dithioethers of phenylalkanes utilized should be sufficient to impart the desired flavor characteristic to the product, but on the other hand, the use of an excessive amount of the derivative is not only wasteful and uneconomical, but in some instances too large a quantity may unbalance the flavor or other organoleptic properties of the product consumed. The quantity used will vary depending upon the ultimate foodstuff; the amount and type of flavor initially present in the foodstuff; the further process or treatment steps to which the foodstuff will be subjected; regional and other preference factors; the type of storage, if any, to which the product will be subject; and the preconsumption treatment, such as baking, frying, and so on, given to the product by the ultimate consumer. Accordingly, the terminology "effective amount" and "sufficient amount" is understood in the context of the present invention to be quantitatively adequate to alter the flavor of the foodstuff.

It is accordingly preferred that the ultimate composition contain from about 0.02 part per million up to about 250 parts per million of gem dithioethers of phenylalkanes or mixtures thereof. More particularly, in food compositions it is desirable to use from about 0.05 to 100 parts per million for enhancing flavors and in certain preferred embodiments of the invention, from about 0.1 to about 10 parts per million of gem dithioethers of phenylalkanes are included to add positive flavors to the finished product.

The amount of gem dithioethers of phenylalkanes or mixtures thereof of our invention to be utilized in flavoring compositions can be varied over a wide range depending upon the particular quality to be added to the foodstuff. Thus, amounts of one or more derivatives according to the present invention of from about 0.5 ppm up to 80 or 90% of the total flavoring composition can be incorporated in such compositions. It is generally found to be desirable to include from about 1 ppm up to about 0.1% of the gem dithioethers of phenylalkanes in such compositions.

The following examples are given to illustrate embodiments of the invention as it is preferred to practice it. It will be understood that these examples are illustrative and the invention is not to be considered restricted thereto except as indicated in the appended claims.

All parts, proportions, percentages and ratios used herein are by weight unless otherwise indicated.

EXAMPLE I

PREPARATION OF ACETOPHENONE DIMETHYL MERCAPTAL

Reaction:

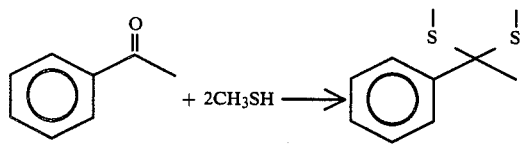

Into a 500 cc reaction flask equipped with stirrer thermometer, gas bubbler and cooling bath is placed 200 ml cyclohexane; 0.5 grams paratoluene sulfonic acid and 19 grams acetophenone. Over a period of 3 hours, 24 grams of methyl mercaptan is bubbled through the gas bubbler into the reaction mass with stirring while maintaining the temperature at 0.5 C. The reaction mass is then continued to be stirred for a period of 8 hours. At the end of the 8 hour period, the reaction mass is fractionally distilled yielding the compound having the structure:

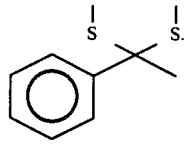

FIG. 1 is the NMR spectrum for the compound having the structure:

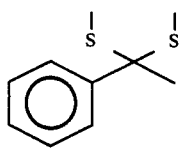

(Conditions: Field strength: 100 MHz; Solvent: CFCl₃).

The compound having the structure:

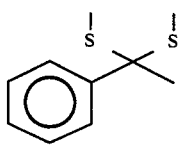

has an onion, durian, tropical fruit, cheesy and sulfury aroma and taste profile at 0.1 ppm causing it to be useful in tropical fruit flavored foodstuffs and cheese and dairy foodstuffs.

EXAMPLE II

PREPARATION OF THE DIMETHYL MERCAPTAL OF HYDROTROPIC ALDEHYDE

Reaction:

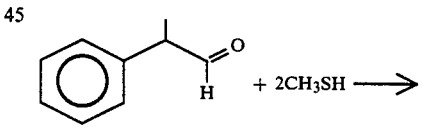

Into a 500 cc flask equipped with stirrer, thermometer, gas bubbler and cooling bath are placed 200 ml methylene dichloride; 0.5 grams paratoluene sulfonic acid; and 26.8 grams of hydratropic aldehyde. While maintaining the reaction mass at 0° C. over a period of 2 hours, 25 grams of methyl mercaptan is bubbled into the reaction mass with stirring. Stirring is continued for a period of 8 hours. At the end of the 8 hour period, the reaction mass is distilled yielding the compound having the structure:

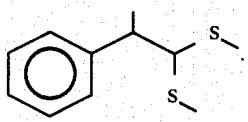

FIG. 2 is the NMR spectrum for the compound having the structure:

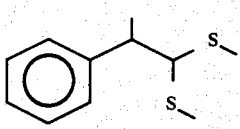

(Conditions: Field strength: 100 MHz; Solvent: CFCl₃).
The compound having the structure:

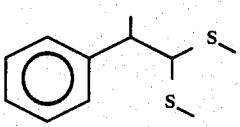

has a beany, raw peanut, cooked vegetable and hydrolyzed vegetable protein-like aroma and taste profile at 0.2 ppm.

EXAMPLE III

The compound having the structure:

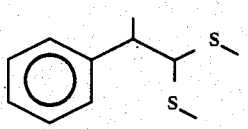

prepared according to Example II is dissolved in propylene glycol to provide a 0.1% solution. The solution in the amount of 0.9 grams is added to 7.3 grams of a soup base consisting of:

| Ingredients | Parts by Weight |
|---|---|
| Fine ground sodium chloride | 35.5 |
| Hydrolyzed vegetable protein | 27.5 |
| Monosodium glutamate | 18.0 |
| Sucrose | 11.0 |
| Beef fat | 5.5 |
| Sethness caramel color (powder B & C) | 2.7 |

The resulting mixture has an excellent beany, cooked vegetable and hydrolyzed vegetable protein-like, beef broth-like aroma and taste with pleasant aesthetically pleasing roasted peanut nuances.

EXAMPLE IV

When the compound having the structure:

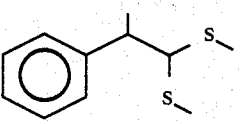

produced according to Example II is added at the rate of 0.5 ppm to H. J. HEINZE ® "Pork'N-BEANS ®", the resulting product has an excellent baked bean and natural cooked bean and pork aroma and taste profile with excellent hydrolyzed vegetable protein-like and natural cooked bean aroma and taste nuances and, in addition, an aesthetically pleasing peanut nuance.

EXAMPLE V

At the rate of 0.5 ppm, the compound having the structure:

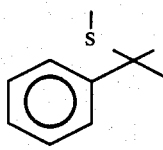

prepared according to Example I is added to GOYA ® Guava Nectar. The resulting guava nectar has a very natural tropical fruit nuance with passion fruit notes imparted to it. A blind bench panel of five members not associated with the instant invention unanimously prefers the Goya Guava Nectar containing the compound having the structure:

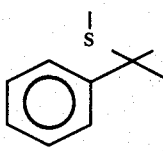

over the guava nectar not containing such compound. The guava nectar not containing the compound having the structure:

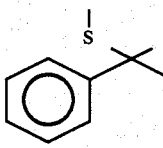

has a tropical fruit, guava flavor but does not have the intense, rich, natural, freshly picked guava nuance contained in the guava nectar containing the compound having the structure:

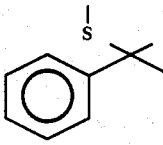

What is claimed is:
1. A process for augmenting or enhancing the aroma or taste of a foodstuff comprising the step of adding to said foodstuff from about 0.05 ppm up to about 250 ppm of a gem dithioether of phenylalkane having the structure:

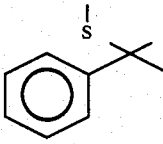

* * * * *